(12) United States Patent
Ishino et al.

(10) Patent No.: US 6,627,910 B2
(45) Date of Patent: Sep. 30, 2003

(54) PRECIPITATION SENSOR

(75) Inventors: Hirotsugu Ishino, Toyohashi (JP); Masao Tokunaga, Gamagori (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 0 days.

(21) Appl. No.: 10/112,049

(22) Filed: Apr. 1, 2002

(65) Prior Publication Data
US 2002/0139944 A1 Oct. 3, 2002

(30) Foreign Application Priority Data
Apr. 2, 2001 (JP) ........................................ 2001-103486

(51) Int. Cl.[7] ............................................. G01N 15/06
(52) U.S. Cl. ................ 250/573; 250/227.29; 356/237.3
(58) Field of Search ................................. 250/573, 574, 250/577, 227.29, 227.11; 356/237.3, 237.2, 445; 340/602, 601, 600, 603, 604; 318/483, 480

(56) References Cited

U.S. PATENT DOCUMENTS 4,701,613 A * 10/1987 Watanabe et al. ........... 340/602
5,661,303 A * 8/1997 Teder ....................... 250/341.8
6,018,165 A 1/2000 Kerkmann et al.
6,147,753 A * 11/2000 Koyama et al. ......... 356/237.3
6,307,198 B1 * 10/2001 Asakura et al. ........ 250/227.25

FOREIGN PATENT DOCUMENTS

JP    A-59-168341    9/1984

* cited by examiner

Primary Examiner—Kevin Pyo
Assistant Examiner—Seung C. Sohn
(74) Attorney, Agent, or Firm—Posz & Bethards, PLC

(57) ABSTRACT

A precipitation sensor has a prism bonded to a front windshield, a beam transmitter, and a beam receiver. The prism has an entry-side prism wall, a connection wall, and an exit-side prism wall. The entry-side prism wall of the prism parallelizes light transmitted from the beam transmitter by refracting them on a convex lens face. The parallelized light is reflected from a parabolic outer face of the prism wall toward the inner face of the windshield. The parallel beams reflected from the inner face of the front windshield are reflected from a parabolic outer face of the exit-side prism wall and then focused on the beam receiver through a convex lens face of the prism wall. The convex shapes of the lens faces form arcs, the centers of which are aligned with the beam transmitter and the beam receiver, respectively.

3 Claims, 3 Drawing Sheets

PRECIPITATION SENSOR

CROSS REFERENCE TO RELATED APPLICATION

This application relates to and incorporates by reference Japanese Patent Application No. 2001-103486 filed on Apr. 2, 2001.

BACKGROUND OF THE INVENTION

This invention relates to a precipitation sensor suitable for use in vehicles.

Referring to FIG. 5, a typical precipitation sensor for use in vehicles is installed on the inner surface of a front windshield W of an automobile and optically detects the presence and absence of precipitation. The precipitation sensor has a prism 1, a beam transmitter 2 and a beam receiver 3. The prism 1 is arranged on the inner surface of the front windshield W as shown and has a prism body 1c integral with plane-convex lens units 1a, 1b, which are formed on its right and left ends. The beam transmitter 2 and the beam receiver 3, which are held by a circuit board 4 located immediately above the prism 1, are opposed to the plane-convex lens units 1a, 1b. A control circuit 5 is mounted on the circuit board 4.

In the precipitation sensor of FIG. 5, the plane-convex lens 1a parallelizes the light beams transmitted from the beam transmitter 2 and guides them into the prism body 1c. The light incident upon the prism body 1c enters the plane-convex lens 1b after it is reflected several times, as shown with the arrows in the figure, between the outer surface of the front windshield W and the center wall of the prism body 1c. The plane-convex lens 1b focuses the light traveling from the prism body 1c and guides the light to the beam receiver 3.

To extend the region used for the detection of precipitation, such a precipitation sensor has an optical path for the sensor light such that the light is reflected several times between the prism 1 and the front windshield W. For this purpose, the beam transmitter 2 and beam receiver 3 have to be mounted beyond the right and left ends of the prism 1. Thus, the dimensions of the precipitation sensor are relatively large in the lateral direction. However, the region for sensing precipitation is too small, even when the light is reflected several times between the prism 1 and the front windshield W in the optical path.

SUMMARY OF THE INVENTION

It is, therefore, an object of the present invention to provide a precipitation sensor in which a prism is shaped to expand the region for precipitation detection and to allow the beam transmitter and beam receiver to be installed between the right and left ends of the prism.

A precipitation sensor according to one aspect of the present invention has a prism (20) to be mounted on an inner surface of a windshield (W), a beam transmitter (40) and a beam receiver (50).

The prism is constructed and arranged to be attached to an inner surface of the windshield. The prism is made with an optically transparent material into a single piece including a connection wall arranged to be bonded to the inner surface of the windshield, and an entry-side prism wall, which is located to be adjacent to the inner surface of the windshield when the sensor is installed. The entry-side prism wall includes a convex entry-side lens surface formed on an inner face, and the entry-side lens surface has an optical axis, which is inclined with respect to the inner surface of the windshield when the device is installed such that the optical axis extends away from the windshield from the entry-side prism wall. The entry-side lens surface forms an arc in a plane parallel to the plane of the windshield, and the center of the arc lies in an entry-side focal point plane that is normal to the plane of the windshield. The entry-side prism wall further includes a parabolic entry-side outer face, and a focal point of the parabolic entry-side outer face lies in the entry-side focal point plane.

The prism further includes an exit-side prism wall, which is arranged to be adjacent to the inner surface of the windshield when the sensor is installed, and the exit side prism wall and the entry-side prism wall are opposed and sandwich the connection wall. The exit side prism wall includes a convex exit-side lens surface, which is generally opposed to the entry-side lens surface, and the exit-side lens surface has an optical axis that is inclined with respect to the windshield such that the optical axis extends away from the inner surface of the windshield from the exit-side lens surface. The exit-side lens surface forms an arc in a plane parallel to the plane of the windshield, and the center of the arc lies in an exit-side focal point plane that is normal to the plane of the windshield. The exit-side prism wall includes a parabolic outer surface, and a focal point of the parabolic outer surface lies in the exit-side focal point plane.

The sensor further includes a beam transmitter, a light emitting part of which is intersected by the entry-side focal point plane. The beam transmitter is located on the optical axis of the entry-side lens surface and is spaced from the entry-side lens face in the direction of the exit-side prism wall such that light transmitted from the beam transmitter is refracted by the entry-side lens surface and such that light entering the entry-side lens surface from the beam transmitter is transmitted by the entry-side prism wall in a parallel manner. When the sensor is installed, parallel light transmitted by the entry-side prism wall enters the windshield and is reflected by the windshield to the exit-side prism wall.

The sensor further includes a beam receiver, a light receiving part of which is intersected by the exit-side focal point plane. The beam receiver is located on the optical axis of the entry-side lens face and is spaced from exit-side lens surface in the direction of the entry-side prism wall, such that light transmitted by the prism wall from the beam transmitter is refracted by the exit-side lens face and focused on the beam receiver.

As described above, the entry-side lens face is convex and arc shaped. The light transmitted from the beam transmitter to the lens face is incident upon the whole area of the lens face in a radiating form. The parallel light entering from the lens face into the prism wall travel toward the outer face in a parallel manner from the entire region of the lens face.

Subsequently, when the parallel light traveling in the entry side prism wall 20b toward the entry-side parabolic outer face is reflected by the parabolic outer face, the light reflected by the outer face travels as a light plane in the prism wall toward the connection wall, because the outer face has the parabolic shape.

The planar incident light beams proceed in a parallel manner toward the connection wall and to the exit-side prism wall, after being reflected by the inner face of the front windshield. When the parallel light is reflected by the exit-side parabolic outer face of the exit-side prism wall, the light reflected by the exit side outer face travels in a parallel manner toward the lens face, because the outer face has the a parabolic shape described above. Then the parallelized light proceeding to the exit-side lens face is refracted by the whole lens face and focused on the beam receiver.

According to the above structure of the optical path for the light transmitted from the beam transmitter, the precipitation detection are is relatively large, even though the beam transmitter and the beam receiver are located between the parabolic outer faces of the prism, and the dimensions of the precipitation sensor are relatively small. This is because the sensor light that passes through the connection wall and enters the front windshield along the optical path is significantly widened two-dimensionally. Also, the decay of the sensor light is low because the light is reflected only once from the inner face of the front windshield. Thus, the efficiency of light transmission is improved.

In the sensor, the optical axes preferably intersect each other at right angles, with the incident angle of the parallel light onto the outer face of the entry-side prism wall being 45 degrees and the incident angle of the parallel light onto the outer face of the exit-side prism wall being 45 degrees.

In another aspect, the invention is a precipitation sensor that is constructed to be attached to the inner surface of a windshield. The sensor includes a light beam transmitter, a light beam receiver, and a prism. The prism includes an entry-side lens surface, and the entry-side lens surface is concave in a plane that is parallel to the plane of the windshield and convex in a plane that is normal to the plane of the windshield. The entry-side lens surface faces the light beam transmitter and the light beam receiver. The sensor further includes an exit-side lens surface, and the exit-side lens surface is concave in a plane that is parallel to the plane of the windshield and convex in a plane that is normal to the plane of the windshield. The exit-side lens surface faces the light beam transmitter and the light beam receiver.

The symbols in the parentheses are exemplary and refer to the specific parts in the illustrated embodiment, which is described below.

DETAILED DESCRIPTION OF THE PREFERRED EMBODIMENTS

Figure 1:
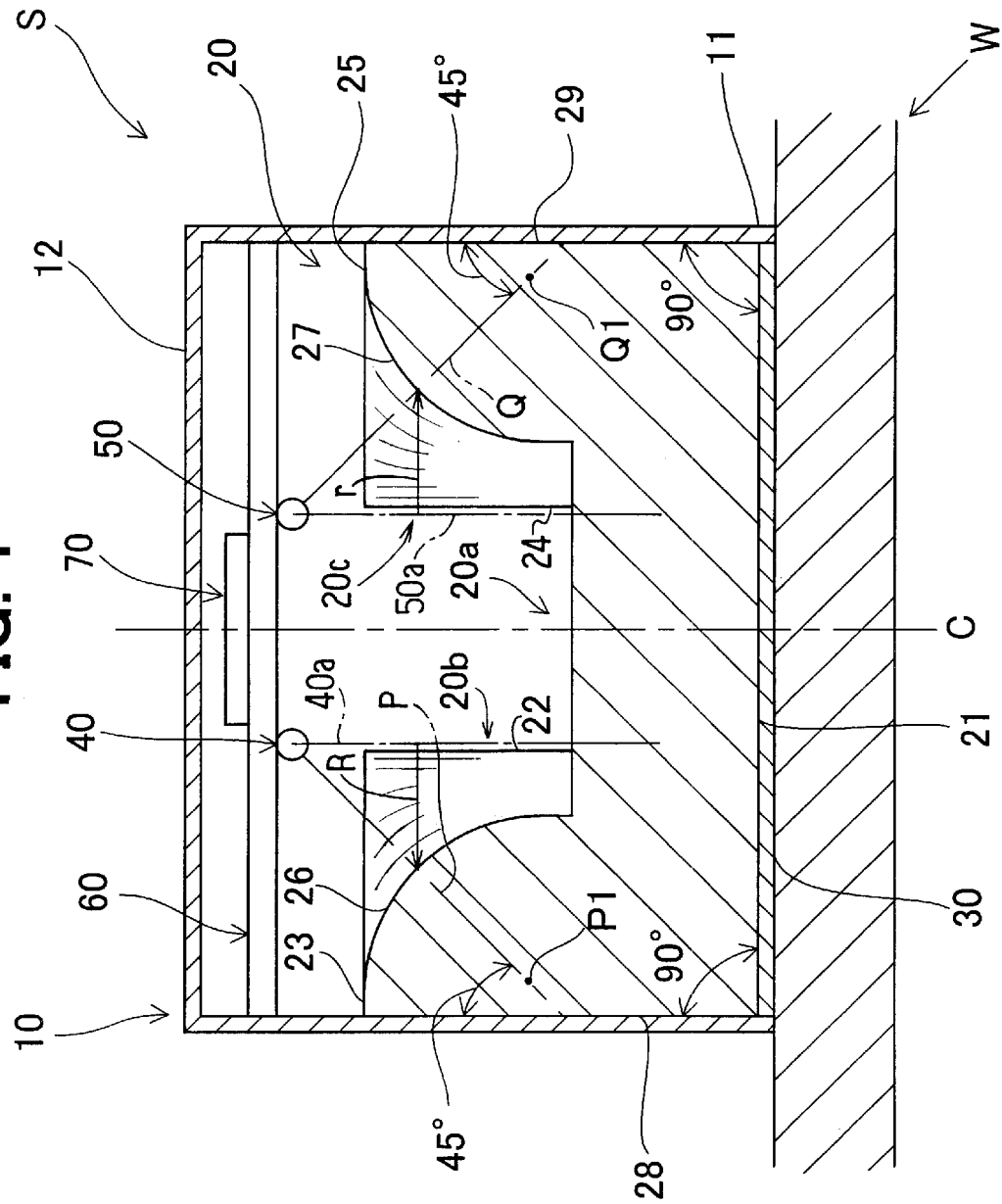
FIG. 1 is a cross-sectional view illustrating a precipitation sensor of the present invention.

A first embodiment of the present invention will be described with reference to FIGS. 1–3. FIG. 1 shows a precipitation sensor S according to the presence invention adapted for use on the front windshield W of an automobile. The precipitation sensor S is connected to an automatic wiper controller for a windshield wiper or a set of windshield wipers (not shown).

The precipitation sensor S is installed on the inner surface of the front windshield W to cover at least a portion of the area wiped by the wiper. The precipitation sensor S optically detects raindrops on the wiper region on the front windshield W and then sends the detection results to the automatic wiper controller.

Referring to FIG. 1, the precipitation sensor S has a prism 20 in a lightproof, or opaque, case 10. The bottom 21 of the prism 20 is adhered to the inner side (in the wiped region) of the front windshield W with a transparent adhesive layer 30 such that the aperture 11 of the case 10 faces the windshield W. In the present embodiment, the right-hand and left-hand sides of the precipitation sensor S in FIG. 1 correspond to the right-hand and left-hand sides of the automobile, respectively.

Referring now to FIG. 1, the precipitation sensor S has a beam transmitter 40 and a beam receiver 50. The beam transmitter 40 and beam receiver 50 are spaced apart and located at a central part of a bottom side of a circuit board 60. The circuit board 60 is fixed to the case 10 and parallel to an upper wall 12 of the case 10. Light emitted of the beam transmitter 40 is directed to an entry-side lens face 26, which will be described later, and the light received by the beam receiver 50 is comes from an exit-side lens face 27, which will be described later. In this embodiment, the beam transmitter 50 is a light emitting diode and the beam receiver 50 is a photodiode. An IC (integrated chip) 70, which is made of a semiconductor chip, is located on the circuit board 60. The IC 70 drives the beam transmitter 40 and processes the output signals provided by the beam receiver 50.

The details of the prism 20 and its relationship to the beam transmitter 40 and the beam receiver 50 are as follows. Referring to FIGS. 1 and 2, the prism 20 has a connection wall 20a, an entry-side prism wall 20b, and an exit-side prism wall 20c, which are formed as a single integral piece. The cross-section thereof has a squared U-shape, and the prism is made of a resin having a high transparency to the light transmitted from the beam transmitter 40. The connection wall 20a is a rectangular solid, a bottom face of which forms the bottom 21 of the prism 20, together with the bottom faces of the entry-side prism wall 20b and exit-side prism wall 20c. The terms "top" and "bottom" are used in this description with reference to the figures, and do not refer to the orientation of the device when installed and in use.

Referring to FIGS. 1 to 4, the entry-side prism wall 20b and the exit-side prism wall 20c, which sandwich the connection wall 20a, extend beyond the upper surface of the connection wall 20a. The entry side prism wall 20b has an inner face 22 and a top face 23, which are perpendicular to each other, and the exit side prism wall 20c has an inner face 24 and a top face 25, which are perpendicular to each other. The inner face 22 of the entry side prism wall 20b is opposed to the inner face 24 of the exit side prism wall 20c. The inner faces 22, 24 are perpendicular to the top face of the connection wall 20a and are spaced apart. The top face 23 of the entry side prism wall 20b is located at the same level as the top face 24 of the exit side prism wall 20c.

Figure 4:
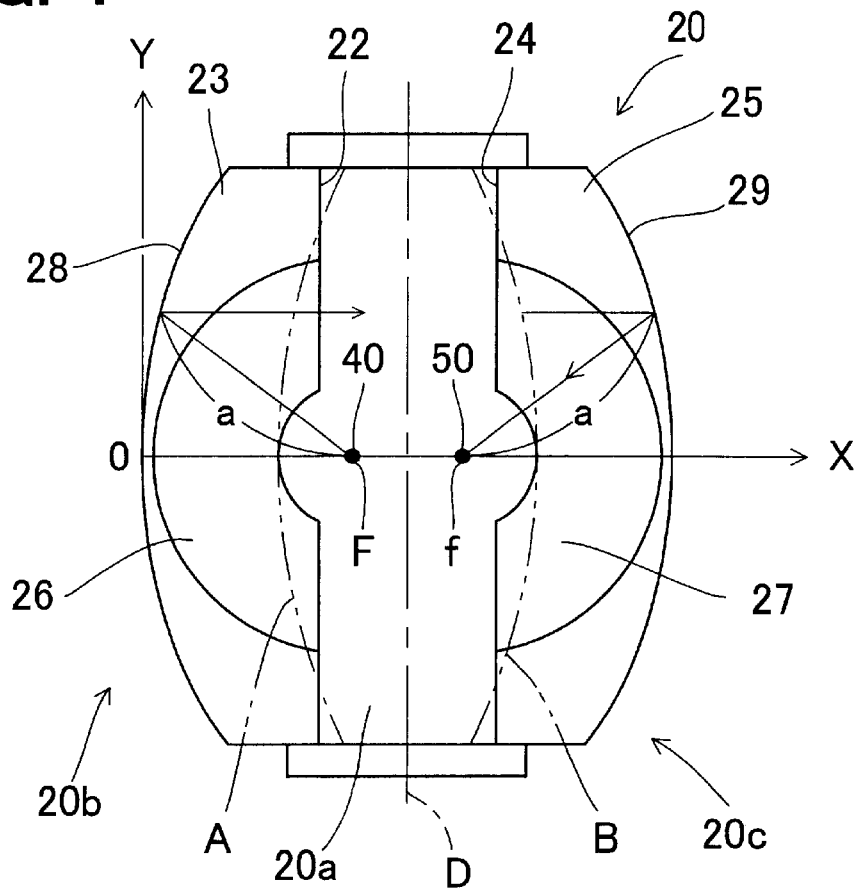
FIG. 4 is a plan view of the prism.
Figure 5:
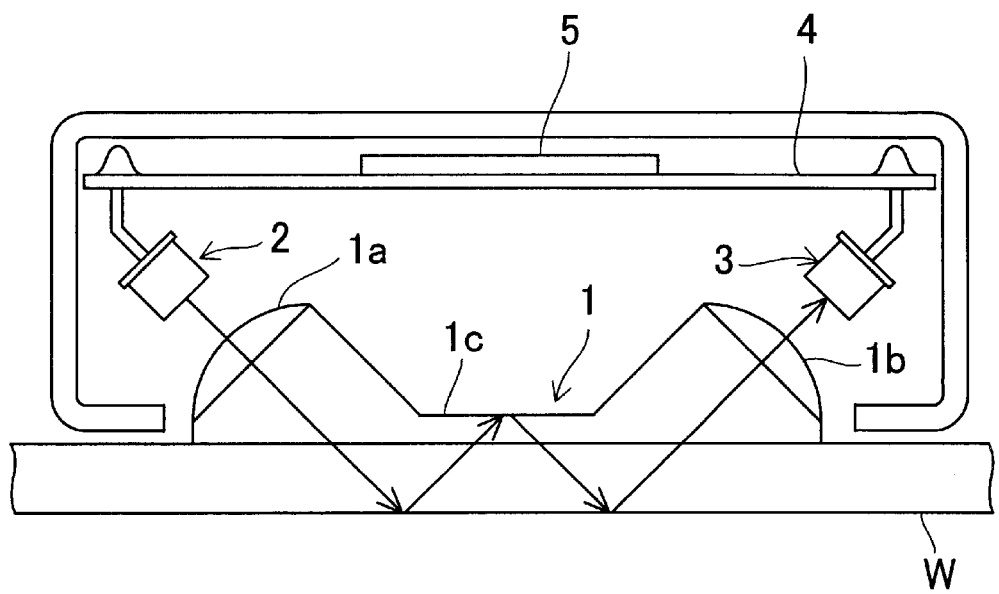
FIG. 5 is a diagrammatic cross-sectional view illustrating a prior art precipitation sensor located on an inner surface of a front windshield.

The entry side prism wall 20b has an entry-side lens face 26, which is opposed to the beam transmitter 40, near the corner where the inner face 22 meets the top face 23. An intersection of the entry-side lens face 26 with a plane parallel to the windshield forms an arc. The arc has a radius of R, and the center of the arc is on a focal point line 40a, which is normal to the plane of the windshield, as shown in FIG. 1 and FIG. 4, and intersects the light emitting part of the beam transmitter 40. Thus, the entry-side lens face 26 is concave in a plane parallel to the plane of the windshield W. The entry-side lens face 26 is convex in a plane that is normal to the plane of the windshield W, as shown in FIG.

1, since the cross sectional plane of FIG. 1 is normal to the plane of the windshield W. The bottom of the entry-side lens face intersects the top surface 20a of the connection wall at a right angle, and the radius R is a minimum when R lies in the plane of the surface 20a.

The location of the focal point of the entry-side lens face 26 is set so that light transmitted from the beam transmitter 40 is parallelized by the entry-side lens face 26 and then proceeds through the entry side prism wall 20b. The radius R varies in the vertical direction of FIG. 1, and the minimum distance between the beam transmitter 40 and the entry side lens face 26 occurs on the axis P (which is the optical axis of the entry-side lens face 26 in the cross-section of FIG. 1). Thus, the intersection of the entry-side lens face 26 with the cross sectional plane of FIG. 1 corresponds to one quarter of a circle, and the top of the entry-side lens face 26 lies at the same level as the top face 23 of the prism and the bottom of the entry-side lens face 26 lies in the same plane as the inner face 24 (see FIG. 1).

The exit side prism wall 20c has an exit side lens face 27, which is opposed to the beam receiver 50, near the corner where the inner face 24 meets the top face 25. The intersection of the exit-side lens face 27 with a plane that is parallel to the plane of the windshield W is an arc, the radius of which is designated by r. Thus, the exit-side lens face 27 is concave in a plane parallel to the plane of the windshield W, as shown in FIG. 4. The center of the arc lies on an exit side focal point line 50a, which intersects the light-receiving part of the beam receiver 50 and is normal to the plane of the windshield, as shown in FIG. 1 and FIG. 4. The exit-side lens face 27 is convex in a cross sectional plane that is normal to the plane of the windshield W, as shown in FIG. 1.

The location of the focal point of the exit-side lens face 27 is set so that parallel light from the exit-side lens face 27 is refracted and focused on the light receiving area of the beam receiver 50. The radius r varies in the vertical direction of FIG. 1, and the minimum distance between the beam receiver 50 and the exit side lens face 27 occurs along the axis Q (the optical axis of the exit-side lens face 27 in the cross-section of the exit side prism wall 20c of FIG. 1) that connects the center Q1 of the arc-shaped surface the exit-side lens face 27 and the light emitting region of the beam receiver 50. Thus the arc shape of the exit-side lens face 27 corresponds to one quarter of a circle, and the top end of the exit-side lens face 27 lies at the same level as the top face 25 of the prism and the bottom of the arc lies in the same plane as the inner face 25 of the prism (see FIG. 1).

The cross-sections of the prism walls 20b, 20c are symmetric with respect to the centerline C in FIG. 1. The beam transmitter 40 and the beam receiver 50 are also located symmetrically with respect to the centerline C. The axes P and Q intersect at right angles in the cross-section of the precipitation sensor S in FIG. 1.

Figure 2:
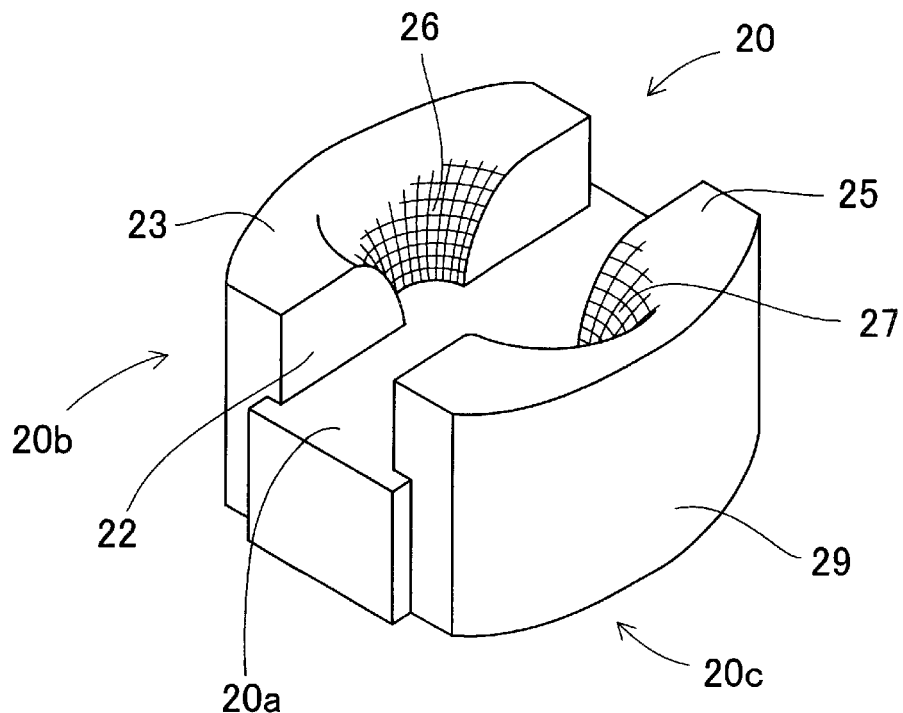
FIG. 2 is a perspective view of a prism of the sensor of FIG. 1.

The entry side prism wall 20b has an entry-side parabolic outer face 28, and the exit side prism wall 20c has an exit-side parabolic outer face 29, as shown in FIG. 2. The entry-side and exit-side outer faces 28, 29 are symmetric with respect to the centerline D in FIG. 4. The shape of the entry-side parabolic outer face 28 is determined so that the parallel light beams traveling from the entry-side lens face 26 into the entry side prism wall 20b are reflected by the outer face 28 in a direction perpendicular to the line D as viewed in FIG. 4.

To be more specific, note FIG. 4, which includes orthogonal X and Y axes. The focal point of the entry-side parabolic outer face 28 is an entry-side focal point F. The entry-side focal point F lies in a plane (the entry-side focal point plane) that is parallel to the inner face 22 of the entry side prism wall 20b and perpendicular to the plane of the windshield. Note that the entry-side focal point plane includes the light emitting area of the beam transmitter 40. That is, as shown in FIG. 4, the entry side focal point F and the light emitting part of the beam transmitter 40 lie on the entry side focal point line 40a, which is normal to the plane of the windshield. The parabolic surface of the entry-side outer face 28 satisfies the relation, $Y=4aX^2$, where a is the distance between the focal point F and the entry-side outer face 28. In the cross-section of the entry side prism wall 20b in FIG. 1, the optical axis P intersects the entry-side outer face 28 at an angle of 45 degrees. Therefore, the parallel light traveling from the lens face 26 into the entry side prism wall 20b proceeds at a reflection angle of 45 degrees toward the inside of the connection wall 20a in a direction perpendicular to the centerline D, as viewed in FIG. 4.

As described above, the entry-side parabolic face 28 and the exit-side parabolic face 29 are symmetric with respect to the centerline D in FIG. 4. The exit-side parabolic surface 29 has a focal point f. The exit-side focal point f is located in a plane that is parallel to the inner face 24 of the exit side prism wall 20c perpendicular to the plane of the windshield. That is, as shown in FIG. 4, the exit-side focal point f and the light receiving part of the beam receiver 50 lie on the exit-side focal point line 50a, which is normal to the plane of the windshield. The exit-side parabolic outer face 29 satisfies the relation, $Y=4aX^2$, where a is the distance between the focal point f and the exit-side parabolic face 29. The optical axis Q intersects the outer face 29 at an angle of 45 degrees in the cross-sectional plane of FIG. 1. Therefore, the parallel light traveling from the connection wall 20a to the exit-side parabolic face 29 proceeds at a reflection angle of 45 degrees toward the exit-side lens face 27 in the direction perpendicular to the centerline D, as viewed in FIG. 4.

In the present embodiment, the light incident upon the outer surface of the front windshield W is totally reflected when there are no raindrops on the wiper region. When there are raindrops on the wiper region, the amount of light reflected from the front windshield decreases accordingly.

Figure 3:
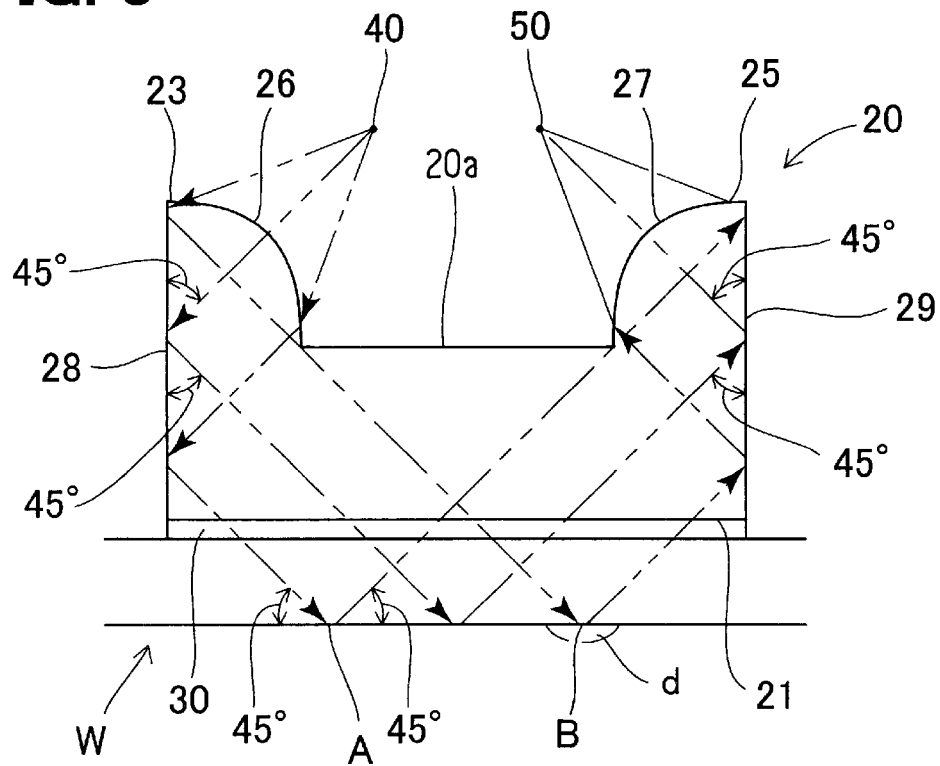
FIG. 3 is a diagrammatic cross sectional view of the precipitation sensor of FIG. 1 with parts removed for illustrative purposes.

When the beam transmitter 40 emits light when driven by the IC 70, the light transmitted from the beam transmitter 40 is incident upon the entry-side lens face 26 of the entry side prism wall 20b as shown by an arrow in FIG. 3. Then, since the focal point of the entry-side lens face 26 is located so that the light transmitted from the beam transmitter 40 is parallelized by the entry-side lens face 26, the light incident upon the entry-side lens face 26 is refracted by the entry-side lens face 26 and travels in a parallel manner toward the entry-side outer face 28 as shown by arrows in FIG. 3.

As described above, the entry-side lens face 26, the cross-section of which is convex in a plane normal to the plane of the windshield, is formed along an arc, the center of which is aligned with the beam transmitter and the radius of which is R. The light beams transmitted from the beam transmitter 40 to the entry-side lens face 26 are incident upon the entire area of the entry-side lens face 26. The parallel light entering from the entry-side lens face 26 into the entry side prism wall 20b travel toward the entry-side outer face 28 in a parallel manner from the whole region of the entry-side lens face 26.

Subsequently, when the parallel light traveling in the entry side prism wall 20b toward the entry-side outer face 28 is reflected by the entry-side outer face 28, the light reflected by the outer face 28 travels in a parallel manner in the entry side prism wall 20b toward the connection wall 20a as shown by arrows in FIG. 3, because the entry-side outer face 28 has a parabolic shape, as described. The parallel light is incident upon the inner face of the front windshield W with the adhesive layer 30 (see the region between broken lines A and B in FIG. 4).

The parallel, incident light proceeds toward the connection wall 20a and the exit side prism wall 20c with the adhesive layer 30 and is reflected by the inner face of the front windshield W. When the parallel light is reflected by the exit-side outer face 29 in the exit side prism wall 20c, the light reflected by the exit-side outer face 29 travels in a parallel manner (as a light plane) toward the exit-side lens face 27, because the exit-side outer face 29 has the parabolic shape described above. Then the parallelized light proceeding to the exit-side lens face 27 is refracted by the entire exit-side lens face 27 and focuses on the light receiving area of the beam receiver 50.

According to the path of light transmitted from the beam transmitter 40, if a raindrop d adheres to the outer surface of the front windshield W as shown in FIG. 3, the amount of light that is reflected from the inner face of the front windshield W, after having reached the inside of the front windshield W through the connection wall 20a and the adhesive layer 30, decreases. Thus, the amount of light that is focused on the beam receiver 50 after passing through the exit-side lens face 27 decreases as well. The control circuit 70 works in accordance with such decreases in light, which are determined by the output of the beam receiver 50.

In this embodiment, a wide region, which is between the two broken lines A, B, is used for the reflection of light that passes through the connection wall 20a and the adhesive layer 30 and enters the front windshield W, even though the beam transmitter 40 and the beam receiver 50 are located between the outer faces 28, 29 of the prism 20. Thus, a wide area is used for detecting precipitation, yet the lateral dimensions of the precipitation sensor are relatively small. Another advantage is that the decay of light intensity is small in the invention because the sensor light is reflected only once from the inner face of the front windshield W. As a result, the efficiency of light that is transmitted from the beam transmitter 40 and received by the beam receiver 50 is relatively high.

The precipitation sensor S according to the present invention may be used not only in automobiles but also other vehicles and ships. Also it may be used with rear and side window glass.

What is claimed is:

1. A precipitation sensor that is constructed to be attached to the inner surface of a windshield, the sensor comprising:
   a light beam transmitter;
   a light beam receiver;
   a prism, the prism including:
      an entry-side lens surface, wherein the entry-side lens surface is concave in a plane that is parallel to the plane of the windshield and convex in a plane that is normal to the plane of the windshield, and the entry-side lens surface faces the light beam transmitter and the light beam receiver; and
      an exit-side lens surface, wherein the exit-side lens surface is concave in a plane that is parallel to the plane of the windshield and convex in a plane that is normal to the plane of the windshield, and the exit-side lens surface faces the light beam transmitter and the light beam receiver, wherein light is transmitted from the light beam transmitter to the light beam receiver through the prism, and water droplets on the outer surface of the windshield are detected based light received by the light beam receiver.

2. A precipitation sensor comprising:
   a prism constructed and arranged to be attached to an inner surface of a windshield, wherein the prism is made with an optically transparent material into a single piece including:
      a connection wall arranged to be bonded to the inner surface of the windshield;
      an entry-side prism wall, which is located to be adjacent to the inner surface of the windshield when the sensor is installed, wherein the entry-side prism wall includes:
         a convex entry-side lens surface formed on an inner face, and the entry-side lens surface has an optical axis, which is inclined with respect to the inner surface of the windshield when the device is installed such that the optical axis extends away from the windshield from the entry-side prism wall, wherein the entry-side lens surface forms an arc in a plane parallel to the plane of the windshield, wherein the center of the arc lies in an entry-side focal point plane that is normal to the plane of the windshield; and
         a parabolic entry-side outer face, wherein a focal point of the parabolic entry-side outer face lies in the entry-side focal point plane;
      an exit-side prism wall, which is arranged to be adjacent to the inner surface of the windshield when the sensor is installed, wherein the exit side prism wall and the entry-side prism wall are opposed and sandwich the connection wall, and the exit side prism wall includes:
         a convex exit-side lens surface, which is generally opposed to the entry-side lens surface, wherein the exit-side lens surface has an optical axis that is inclined with respect to the windshield such that the optical axis extends away from the inner surface of the windshield from the exit-side lens surface, wherein the exit-side lens surface forms an arc in a plane parallel to the plane of the windshield, wherein the center of the arc lies in an exit-side focal point plane that is normal to the plane of the windshield; and
         a parabolic outer surface, wherein a focal point of the parabolic outer surface lies in the exit-side focal point plane;
      a beam transmitter, a light emitting part of which is intersected by the entry-side focal point plane, is located on the optical axis of the entry-side lens surface and spaced from the entry-side lens face in the direction of the exit-side prism wall such that light transmitted from the beam transmitter is refracted by the entry-side lens surface and such that light entering the entry-side lens surface from the beam transmitter is transmitted by the entry-side prism wall in a parallel manner, wherein, when the sensor is installed, parallel light transmitted by the entry-side prism wall enters the windshield and is reflected by the windshield to the exit-side prism wall;
      a beam receiver, a light receiving part of which is intersected by the exit-side focal point plane, is located on the optical axis of the entry-side lens face, the beam receiver being spaced from exit-side lens surface in the direction of the entry-side prism wall, such that light transmitted by the prism wall from the beam transmitter is refracted by the exit-side lens face and focused on the beam receiver.

3. The precipitation sensor according to claim 2, wherein the optical axes intersect each other at right angles, and light transmitted from the beam transmitter through the entry-side prism wall has an angle of incidence to the entry-side outer parabolic face of 45 degrees, and light transmitted from the beam transmitter and reflected by the windshield approaches the exit-side outer parabolic face with an angle of incidence of 45 degrees.

* * * * *